United States Patent
Chhatwal et al.

(10) Patent No.: US 8,956,612 B2
(45) Date of Patent: Feb. 17, 2015

(54) PEPTIDE ASSOCIATED WITH RHEUMATIC FEVER (PARF) AND ITS USE AS A DIAGNOSTIC MARKER

(75) Inventors: Gursharan S. Chhatwal, Denkte (DE); Patric D. Nitsche-Schmitz, Braunschweig (DE); Katrin Dinkla, Braunschweig (DE); Vanessa Barroso, Essex (GB)

(73) Assignee: Helmholtz-Zentrum für Infektionsforschung GmbH, Braunschweig (DE)

( * ) Notice: Subject to any disclaimer, the term of this patent is extended or adjusted under 35 U.S.C. 154(b) by 1557 days.

(21) Appl. No.: 12/302,969

(22) PCT Filed: Jun. 1, 2007

(86) PCT No.: PCT/EP2007/004898
§ 371 (c)(1), (2), (4) Date: Jan. 22, 2010

(87) PCT Pub. No.: WO2007/140953
PCT Pub. Date: Dec. 13, 2007

(65) Prior Publication Data
US 2010/0150929 A1    Jun. 17, 2010

(30) Foreign Application Priority Data
Jun. 6, 2006  (EP) ..................... 06011685

(51) Int. Cl.
| | | |
|---|---|---|
| *A61K 39/40* | (2006.01) | |
| *C07K 16/12* | (2006.01) | |
| *C07K 14/315* | (2006.01) | |
| *A61K 38/00* | (2006.01) | |
| *A61K 39/00* | (2006.01) | |

(52) U.S. Cl.
CPC ........... *C07K 16/1275* (2013.01); *C07K 14/315* (2013.01); *A61K 38/00* (2013.01); *A61K 39/00* (2013.01); *A61K 2039/53* (2013.01)
USPC ............. 424/150.1; 424/165.1; 530/387.1

(58) Field of Classification Search
None
See application file for complete search history.

(56) References Cited

U.S. PATENT DOCUMENTS
6,280,997 B1   8/2001  Eriksson et al.
7,041,442 B1   5/2006  Kern et al.

FOREIGN PATENT DOCUMENTS
WO    WO 00/75180    12/2000
WO    WO 03/033520   4/2003

OTHER PUBLICATIONS

Greenspan et al (Nature Biotechnology 7: 936-937, 1999).*
Chothia et al (The EMBO Journal, 1986, 5/4:823-26).*
Mikayama et al. (Nov. 1993. Proc.Natl.Acad.Sci. USA, vol. 90: 10056-10060).*
Rudinger et al. (Jun. 1976. Peptide Hormones. Biol.Council. pp. 5-7).*
Rudikoff et al (Proc Natl Acad Sci USA 1982 vol. 79 p. 1979).*
Wu et al. J. Mol. Biol. (1999) 294, 151-162.*
Dinkla, K. et al., "Rheumatic fever-associated *Streptococcus pyogenes* isolates aggregate collagen," *The Journal of Clinical investigation*, Jun. 2003, vol. 111, No. 12, pp. 1905-1912.
Frank, R., "Spot-synthesis: An Easy Technique for the Positionally Addressable, Parallel Chemical Synthesis on a Membrane Support," *Tetrahedron*, 1992, vol. 48, No. 42, pp. 9217-9232.
Kumar, D. et al., "An easy method for detection of rheumatic antigen(s) in rheumatic fever/rheumatic heart disease patients by dot-ELISA," *Can. J. Cardiol.* 1998, vol. 14, No. 6, pp. 807-810.
Reißmann et al., "Region Specific and Worldwide Distribution of Collagen-Binding M Proteins with PARF Motifs among Human Pathogenic Streptococcal Isolates", *PLoS ONE*, 2012, vol. 7, No. 1, e30122, pp. 1-11.

* cited by examiner

*Primary Examiner* — Jennifer Graser
(74) *Attorney, Agent, or Firm* — Saliwanchik, Lloyd & Eisenschenk

(57) ABSTRACT

The present invention relates to a streptococcal octapeptide AXYLXXLN, and preferably to the octapeptide AXYLZZLN, designated as peptide associated with rheumatic fever (PARF) that, through its interaction with human collagen, plays a crucial role in the pathogenesis of rheumatic fever. PARF therefore represents a marker for rheumatic fever associated strains and provides a target for therapies, and in particular preventive therapies.

6 Claims, 4 Drawing Sheets

A

B

A

B

C

A

Figure 1:
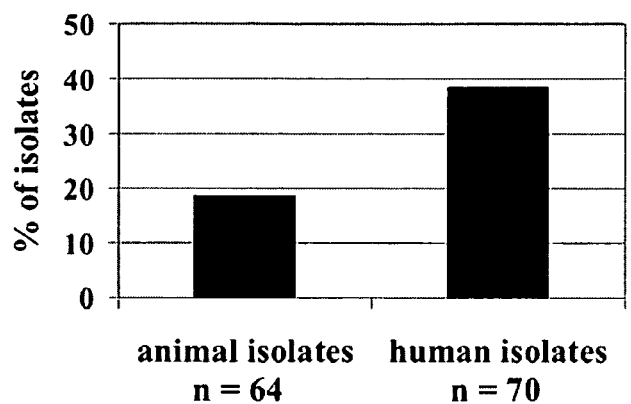
Figure 1:
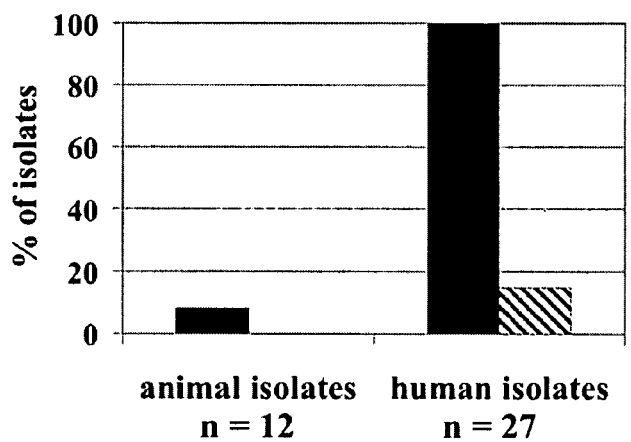

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|
| 26 | 27 | 28 | 29 | 30 | 31 | 32 | 33 | 34 | 35 | 36 | 37 | 38 | 39 | 40 | | | | | | | | | | |

B

| SEQ ID NO: 16 | 17 | KQNNSIGEYARYLQK |
| SEQ ID NO: 17 | 18 | NSIGEYARYLQKLND |
| SEQ ID NO: 18 | 19 | GEYARYLQKLNDQFQ |
| SEQ ID NO: 19 | 20 | ARYLQKLNDQFQEYY |

C / D

| | | SEQ ID NO.: |
|---|---|---|
| 41 | GEYARYLQKLNAQFQ | 20 |
| 42 | GEYARYLQKLADQFQ | 21 |
| 43 | GEYARYLQKANDQFQ | 22 |
| 44 | GEYARYLQALNDQFQ | 23 |
| 45 | GEYARYLAKLNDQFQ | 24 |
| 46 | GEYARYAQKLNDQFQ | 25 |
| 47 | GEYARALQKLNDQFQ | 26 |
| 48 | GEYAAYLQKLNDQFQ | 27 |
| 49 | GEYDRYLQKLNDQFQ | 28 |
| 50 | GEYRDLKLQAYNQFQ | 29 |

$^{56}$GEY ARYLQKLND QFQ$^{69}$

SEQ ID NO: 30

E

```
            10         20         30         40         50         60         70
FOG  DRWKAQTEEARTDKLIAGFANLDADVTNLGKMMDELQKLKDFSKQNNSIGEYARYLQKLNDQFQ   SEQ ID NO: 31
         ... :  :  ::   ::  .::.:   .    .  .::.:  ...:.  :.::. :::
M3   DARSVNGEFPRHVKLKNEIENLLDQVTQLYTKHNSNYQQYNAQAGRLDLRQKAEYLKGLNDWAE   SEQ ID NO: 32
            10         20         30         40         50         60

80         90         100        110        120
FOG  EYYEQVVGDDSRRVLAKELAKNTELNEKLSELSTTSQALAKELQEQKENYDLVK              SEQ ID NO: 31 (cont'd)
       . ...  :.:  ..::.:   ..  .:......::.    .    :: :.  ...::.:
M3   RLLQELNGEDVKKVLGKVAFEKDDLEKEVKELKEKIDKKEKEYQDLDKDFDLAK              SEQ ID NO: 32 (cont'd)
            70         80         90         100        110
```

F

| Protein | Dot Blot | SPR |
|---|---|---|
| FOGfl | +++ | +++ |
| E$^{56}$→A | +++ | ++ |
| A$^{58}$→D | + | − |
| Y$^{60}$→A | − | − |
| L$^{61}$→A | ++ | + |
| L$^{64}$→A | − | − |
| N$^{65}$→A | − | − |
| D$^{66}$→A | ++ | ++ |
| LND$^{66}$→AAA | − | − |
| YL$^{61}$→AA | − | − |

G AXYLZZLN

SEQ ID NO: 2

FIG. 4

PEPTIDE ASSOCIATED WITH RHEUMATIC FEVER (PARF) AND ITS USE AS A DIAGNOSTIC MARKER

This application is a National Stage Application of International Application Number PCT/EP2007/004898, filed Jun. 1, 2007; which claims priority to European Patent Application No. 06011685.2, filed Jun. 6, 2006, all of which are incorporated herein in their entirety.

The present invention relates to a streptococcal octapeptide AXYLXXLN, and particularly the octapeptide AXYLZZLN, designated as peptide associated with rheumatic fever (PARF) that, through its interaction with human collagen, plays a crucial role in the pathogenesis of rheumatic fever. PARF therefore represents a marker for rheumatic fever associated strains and provides a target for therapies, and in particular preventive therapies.

For the purposes of the present invention, all references as cited herein are incorporated by reference in their entireties.

BACKGROUND OF THE INVENTION

Acute rheumatic fever and the subsequent rheumatic heart disease are serious sequelae of streptococcal infections. It has been known for decades that *Streptococcus pyogenes* infection is a cause of this sequelae, but only recently it has been shown that other streptococcal species can also induce acute rheumatic fever in humans.

Acute rheumatic fever (ARF) is one of the most serious diseases caused by streptococci and occurs as an autoimmune sequela following untreated or inadequately treated *S. pyogenes* pharyngitis (A. L. Bisno, N Engl J Med 325, 783 (Sep. 12, 1991), M. McDonald, B. J. Currie, J. R. Carapetis, Lancet Infect Dis 4, 240 (April 2004)). ARF and the subsequent rheumatic heart disease (RHD) remain significant causes of cardiovascular disease today (WHO, "Rheumatic fever and rheumatic heart disease—Report of an Expert Panel" (2004)). The most devastating effects are on children and young adults in their most productive years. According to a recent estimate more than 15 million people have RHD, more than 0.5 million acquire ARF each year, and about 0.25 million deaths annually are directly attributable to ARF or RHD (J. R. Carapetis, M. McDonald, N. J. Wilson. Lancet 366, 155 (Jul. 9-15, 2005)).

A number of different autoimmune mechanisms have been proposed for pathogenesis of ARF (M. W. Cunningham, Clin Microbiol Rev 13, 470 (July 2000)). One recent hypothesis is that the *S. pyogenes* strains. which have a potential of causing ARF, interact with human collagen and form an aggregated complex that acts as an autoantigen. The sera of patients with ARF or RHD show significantly higher titers of anticollagen antibodies compared to control sera of healthy donors. An *S. pyogenes* surface protein, M3 protein, and hyaluronic acid capsule (HA) were identified as streptococcal components that interact with and aggregate collagen. Immunization of mice with purified M3 protein led to the generation of anticollagen antibodies. Direct binding of collagen to streptococcal surface components is therefore considered as one of the key mechanisms for induction of ARF (K. Dinkla et al., J Clin Invest 11 1, 1905 (June 2003)).

In geographical areas with high incidence of ARF there is a widespread carriage of group C streptococci (GCS) and group G streptococci (GGS) (for references, see M. McDonald, B. J. Currie, J. R. Carapetis, Lancet Infect Dis 4, 240 (April 2004)). Traditionally, these serogroups are considered as important veterinary pathogens, but are also involved in human infections. Recently it has been shown that carriage of GCS and GGS may lead to induction of ARF in humans (A. Haidan et al., Lancet 356,1167 (Sep. 30, 2000)).

The fact that penicillin has clearly failed to eradicate ARF and streptococcal vaccines are still years away from being available underlines the need for novel control strategies (E. L. Kaplan, Heart 91, 3 (January 2005)).

It is well known that some *S. pyogenes* strains are more likely to cause ARF than others (G. H. Stollerman, Clin Immunol Immunopathol 61, 131 (November 1991)).

WO 2004-071422 describes *S. pyogenes* serum opacity factor (SOF)- and *S. dysgalactiae* fibronectin-binding protein-based polypeptides, and antibody compositions and methods. The compositions are regarded as effective in eliciting opsonic and/or protective antibodies specific for *S. pyogenes* and/or *S. dysgalactiae* and, consequently, as useful for the treatment, diagnosis, and monitoring of streptococcal infections, including *S. pyogenes* and *S. dysgalactiae* infections, and diseases associated with *S. pyogenes* and *S. dysgalactiae* infections, as well as associated autoimmune neurological disorders.

WO 03/033520 A2 describes cyclic peptides that are different from the ones of the present invention.

JP 10262698 describes a probe including a DNA fragment derived from *S. pyogenes* as a probe for diagnosing an infectious disease. The probe is describes as useful for detection and identification of the *S. pyogenes*, which is a pathogen of pharyngitis, rheumatic fever, nephritis, erysipelas, scarlatina, septicemia, etc. The probe is obtained by extracting a chromosome DNA from the *S. pyogenes* microbe, allowing the extracted chromosome DNA to be completely digested by a restriction enzyme Hind III, cloning the digested DNA and selecting a fragment manifesting a specific reactivity with the DNA of the microbe.

U.S. Pat. No. 6,777,547 describes collagen-binding proteins Cpa1 and Cpa49 from *S. pyogenes*, and their corresponding amino acid and nucleic acid sequences as useful in the prevention and treatment of infection caused by group A streptococcal bacteria such as *S. pyogenes*. These proteins have been observed to bind to collagen, and methods are provided, such as by administration of the proteins or antibodies generated thereto, whereby streptococcal binding of collagen can be inhibited, and streptococcal infection can be greatly reduced. In particular, the proteins are described as being advantageous because they may be used as vaccine components or antibodies thereof, and they may be administered to wounds or used to coat biomaterials in order to act as collagen blocking agents and reduce or prevent severe infection by group A streptococcal bacteria. Cpa1 and Cpa49 are homologs of the collagen binding proteins CNA from *Staphylococcus aureus* and CNE from *Streptococcus equi*, and bind collagen through a mechanism that is different from PARF.

Kumar D et al (in Kumar D, Kaur S, Grover A, Singal P K, Ganguly N K. An easy method for detection of rheumatic antigen(s) in rheumatic fever/rheumatic heart disease patients by dot-ELISA. Can J Cardiol. 1998 June; 14(6):807-10) describe various monoclonal antibodies developed against human B cell alloantigen, e.g. the monoclonal antibody D8/17 which was found to be 100% specific for rheumatic fever/rheumatic heart disease patients from New York, but which identified only 62% to 68% in the north Indian population.

An early diagnosis of "rheumatogenic strains" is indispensable for risk-assessment of primary infection. A prerequisite for the development of diagnostic and preventive approaches is an understanding of pathogenic mechanisms underlying ARF. Despite the above progresses, still further and effective options for the treatment and the diagnosis of infections caused by bacteria that contain M- or M-like proteins, and in particular streptococcal bacteria are sought for. It is therefore an object of the present invention, to provide effective means in order to fulfill those needs. Other objects, features and advantages of the present invention will be set forth in the detailed description of preferred embodiments that follows, and in part will be apparent from the description or may be learned by practice of the invention. These objects and advantages of the invention will be realized and attained by the methods and compositions particularly pointed out in the written description and claims hereof.

According to the present invention, the object of the present invention is solved by providing a collagen binding peptide comprising the sequence AXYLXXLN (SEQ ID No. 1) wherein X can be any naturally occurring amino acid, provided that the peptide is not an intact bacterial M- or M-like protein, i.e. provided that the peptide is not the intact bacterial polypeptide from which the amino acid sequence is derived (i.e. one of the full-length sequences of M- or M-like proteins as described in the literature). Preferred is a collagen binding peptide comprising the sequence AXYLZZLN (SEQ ID No. 2) wherein X and Z can be any naturally occurring amino acid, and at least one of Z is occupied by a basic amino acid, preferably lysine or arginine or a chemically modified variant thereof, provided that the peptide is not an intact bacterial M- or M-like protein.

Further preferred is a collagen binding peptide according to the present invention, wherein said peptide consists or essentially consists of the amino acid sequence according to SEQ ID No. 3 to SEQ ID No. 15, or a chemically modified variant thereof The following table shows the preferred PARF-peptides of the present invention, as well as their origins (full length-proteins, together with database Accession numbers). As can be seen from the sequences, position 1 appears to be rather flexible, whereas position 3, 4, 7 and 8 are highly conserved and important for an efficient binding of collagen:

| Protein | Database Accession No. | Sequence | SEQ ID No. | Species |
|---|---|---|---|---|
| FOG | AAT99868 | ARYLQKLN | SEQ ID No. 3 | Streptococcus dysgalactiae subsp. equisimilis |
| M3 | BAA03311 | AEYLKGLN | SEQ ID No. 4 | Streptococcus pyogenes |
| emmLC1903 | AY686728 | AEYLQRLN | SEQ ID No. 5 | Streptococcus dysgalactiae subsp. equisimilis |
| emmLC1904 | AAU26048 | AEYLQRLN | SEQ ID No. 6 | Streptococcus constellatus |
| st4545 | AAC27085 | AWYLKELN | SEQ ID No. 7 | Streptococcus dysgalactiae subsp. equisimilis |
| NS31 | AAY30314 | ARYLETLN | SEQ ID No. 8 | Streptococcus dysgalactiae subsp. equisimilis |
| NS15 | AAY30313 | AEYLKALN | SEQ ID No. 9 | Streptococcus dysgalactiae subsp. equisimilis |
| M55 | CAA50980 | ATYLKELN | SEQ ID No. 10 | Streptococcus pyogenes |
| emmG1 | AAA26928 | AQYLRELN | SEQ ID No. 11 | Streptococcus dysgalactiae subsp. equisimilis |
| g0emmL | AAA67071 | EAYLKRLN | SEQ ID No. 12 | Streptococcus dysgalactiae subsp. equisimilis |
| stC2sk.0 | ABE77389 | TQYLKRLN | SEQ ID No. 13 | Streptococcus dysgalactiae subsp. equisimilis |
|  | AAC84045 | TQYLKRLN | SEQ ID No. 14 | Streptococcus dysgalactiae subsp. equisimilis |
| G40M |  | ARYLKRLN | SEQ ID No. 15 | Streptococcus dysgalactiae subsp. equisimilis |

"Consisting essentially of" shall mean that a peptide according to the present invention, in addition to the sequence according to any of SEQ ID No. 1 to SEQ ID No. 15 or a chemically modified variant thereof, contains additional N- and/or C-terminally located stretches of amino acids that are not necessarily forming part of the peptide that functions as collagen binding sequence as defined herein.

In the context of the present invention, the inventors investigated the potential of different streptococcal species to interact with and to aggregate collagen, in order to understand the underlying mechanisms and to identify the involved bacterial components. A total of 134 GCS and GGS strains, out of which 64 were isolated from animals and 70 from human infections, were included in this study. An S. pyogenes strain with high rheumatogenic potential was included as a positive control (J. R. Carapetis, M. McDonald, N. J. Wilson. Lancet 366, 155 (Jul. 9-15, 2005)). All strains were tested for binding to radioactive collagen.

Nineteen percent of the animal isolates and 38 percent of the human isolates had the ability to bind collagen (FIG. 1A). The highest frequency (48 percent) of the collagen binding ability was found in human GGS. However, none of the animal GGS interacted with collagen. All isolates found positive for collagen binding were tested for the presence of emm or emm-like genes by PCR using primers of highly conserved sequences.

U.S. Pat. No. 6,280,997 discloses a collection of 1166 protein sequences, wherein the shortest peptide has a length of 30 amino acids. None of these peptides were reported to have collagen binding activity.

Dinkla et al. (2003) Clin Invest 111, 1905-1912 disclose that the M3 protein of S. pyogenes is responsible for the aggregation of collagen type IV. Nevertheless, it was found that PARF is not only present in M3 of *S. pyogenes* but also in FOG of *S. dysgalactiae* and in other M- or M-like proteins. Dinkla et al. further hypothesize that structural reorganisations in the collagen is the reason for the autoimmune response. Nevertheless, it has been proven in the present invention that the interaction of collagen with a protein carrying a PARF-motif is required.

All human isolates possessed emm- or emm-like genes, whereas only one animal isolate was found positive (FIG. 1B). In this isolate, HA capsule was responsible for collagen binding because its specific degradation abolished the interaction with collagen. In all strains which interacted with collagen the presence of collagen binding factors, such as HA capsule from *S. pyogenes*, the collagen binding protein CNE from *S. equi* (J. Lannergard, L. Frykberg, B. Guss, FEMS Microbial Lett 222, 69 (May 16, 2003)) and the M-like protein FOG (fibrinogen binding protein of GGS) (H. M. Johansson, M. Morgelin, I. M. Frick, Microbiology 150, 421 1 (December 2004), D. P. Nitsche, H. M. Johansson, I. M. Frick, M. Morgelin, J Biol Chem 281, 1670 (Jan. 20, 2006)), was investigated. HA was found in 30 percent of the isolates and was distributed equally among human GGS, human GCS and animal GCS. CNE was found only in animal GCS, whereas FOG was expressed by human GGS isolates only (FIG. 1B), consistent with a previous report (W. J. Simpson, J. C. Robbins, P. P. Cleary, Microb Pathog 3, 339 (November 1987)). The interaction of streptococci with collagen was also analyzed using scanning electron microscopy. This analysis led to the interesting observation, that FOG-positive human isolates bound collagen and also aggregated it. None of the animal isolates which interacted with collagen caused any aggregation (FIG. 2A, 2B). For further investigation, three different recombinant proteins FOGfl (aa 1-557), FOG1-B (aa 1-278), and FOG1-A (aa 1-134) were used (FIG. 2C).

The binding of shorter fragments FOG1-B and FOG1-A, examined by surface plasmon resonance (SPR) measurement indicated concentration dependent interaction with immobilized collagen IV (FIGS. 2D and 2E). Coherent with data on collagen I (D. P. Nitsche, H. M. Johansson, I. M. Frick, M. Morgelin, J Biol Chem 281, 1670 (Jan. 20, 2006)), these experiments indicated that the N-terminal region of FOG is the major collagen binding component of human GCS and GGS.

In case of *S. pyogenes* the surface protein M3 binds and aggregates collagen, leading to collagen IV auto-antigenicity (K. Dinkla et al., J Clin Invest 11 1, 1905 (June 2003)). The present inventors therefore immunized mice with the N-terminal region of M3 protein (M3.5, aa 1 to aa 186) and with FOG fragments 1-A and 1-B. Substantially higher titers of anti-collagen antibodies were observed in ELISA, with sera from M3 protein and FOG fragments immunized mice as compared to the buffer control (FIG. 3A). To determine the specificity of the antibodies, the collagen IV reactive mouse sera were pooled and antibodies against collagen IV and FOG1-A were determined before and after pre-absorption with FOG protein. The serum titer against collagen IV remained almost unchanged after preabsorption, indicating lack of any cross-reactivity between anti-FOG and anti-collagen antibodies (FIG. 3B). To further confirm the auto-antigenicity of FOG-collagen complex, sera from patients with ARF and healthy controls were tested for reactivity against N-terminal of M3 protein as well as FOG1-A. A six- to eight-fold increase of serum titers against FOG1-A was observed with patients' sera as compared to control sera from healthy donors from the same geographic region (FIG. 3C).

To map the domain of FOG protein responsible for interaction with collagen, 15 mer peptides were synthesized on a membrane (R. Frank, Tetrahedron 48, 9217 (1992)), constituting a 3 amino acid shift that represents the sequence of FOGI-A. Radiolabeled collagen IV as a soluble ligand was tested for binding to the membrane-bound peptides. A strong signal was obtained with peptide 17 to 20 containing the common sequence ARYLQK (FIG. 4A, 4B). The sequence of peptide 19 was selected for mutational analysis, where different amino acids were substituted before synthesis on the membrane (FIG. 4C). The binding analysis indicated that the sequence ARYL-K is essential for interaction of the synthetic peptides with collagen IV (FIG. 4D). Sequence comparison revealed considerable homology in the N-terminals of FOG1-A and M3 protein (25.4% identity, 118 aa overlap). Notably, the collagen binding peptide of FOG belongs to a patch of conserved amino acids (FIG. 4E) that are present in all 15 known subtypes of M3.

To examine the collagen binding property of this motif in its native structural environment site-directed substitution of the amino acids conserved between FOG and M3 was performed to generate mutants of the full length protein FOGfl. Collagen binding of the mutants was compared with the wild type protein in dot blot and surface plasmon resonance analysis. Substitution of $A^{58}$, $Y^{60}$, $L^{64}$, $N^{65}$, $LND^{66}$ and $YL^{61}$ (aa numbers based on the FOGfl full-length sequence) completely abolished collagen binding (FIG. 4F). The results of spot membrane and site-directed mutagenesis led to the identification of an octa-peptide AXYLXXLN, preferably AXYLZZLN, as a binding and aggregating component of collagen (FIG. 4G). Searching in the public data bases revealed several other M-proteins that contained such sequences, among those type G1, stg4545, emmLC1903, and emmLC1904 from GGS and M55 from GAS. To test the prediction of the present inventors, a GCS-strain of emm-type emmLC1903 (AEYLQRLN) was examined and found positive for collagen binding. In both, FOG and M3 one of the positions denoted by Z is occupied by lysine (FIG. 4E) in emmLC1903 lysine is replaced by arginine, which has a similar character. Alanine-substitution demonstrated that $K^{63}$ was important for an efficient interaction of the synthetic peptide 19 (FIGS. 4C and D), suggesting that lysine in one of the Z-positions is beneficial for the collagen binding motif. Binding of collagen IV to GCS type emmLC1903 indicates that lysine can be substituted by arginine, without a loss of collagen binding.

The motif described above plays a crucial role in rendering collagen an auto-antigen and subsequently in pathogenesis of rheumatic fever. The peptide was therefore designated PARF (peptide associated with rheumatic fever). Since PARF is present not only in the surface protein of group A streptococci, but also in group C and G streptococci, the role of the GCS and GGS in rheumatic fever is now understandable. The results of this study have made clear hat the induction' of rheumatic fever cannot be uniquely associated with group A streptococcal infections, and that other streptococcal species play an equivalent or even more important role in the pathogenesis of rheumatic fever. These results have important diagnostic and therapeutic consequences.

The peptides according to the invention can have an overall length of between 8 and 100, preferably between 8 and 30, and most preferred between 8 and 12 amino acids. Furthermore, at least one peptide according to any of SEQ ID No. 1 to SEQ ID No. 15 can include non-peptide bonds. Furthermore, the respective nucleic acids can encode for between 8 and 100, preferably between 8 and 30, and most preferred between 8 and 12 amino acids. Most preferred are peptides according to SEQ ID No. 3 to SEQ ID No. 15 or a chemically modified variant thereof.

In the context of the present invention, a "chemically modified variant" shall mean a peptide, wherein the amino acids of the sequence have been modified to include additional chemical moieties. Usually, this modification is performed in vitro and introduces chemical groups, such as dyes, linkers, spacers, enzymes, and the like, that allow for improved handling of the peptides (such as coupling to a solid phase or dye-based reaction) or the more effective generation of antibodies (such as with poly-lysine-moieties). The chemically modified variant of the peptide according to the invention will have substantially the same conformation and/or function (i.e. confers collagen binding), as the non-modified peptide according to the invention.

In a further preferred embodiment thereof, the invention provides a collagen binding peptide, wherein said peptide includes non-peptide bonds.

By "peptide" the inventors include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159,3230-3237, incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis.

Peptides (at least those containing peptide linkages between amino acid residues) may be synthesized by the Fmoc-polyamide mode of solid-phase peptide synthesis as disclosed by Lu et al (1981) J. Org. Chem. 46, 3433-3436, and references therein. Temporary N-amino group protection is afforded by the 9-fluorenylmethyloxycarbonyl (Fmoc) group. Repetitive cleavage of this highly base-labile protecting group is achieved by using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethylphenoxyacetic acid derivative. All amino acid derivatives are added as their preformed symmetrical anhydride derivatives with the exception of asparagine and glutamine, which are added using a reversed N,N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesized.

Trifluoroacetic acid is removed by evaporation in vacuo, with subsequent trituration with diethyl ether affording the crude peptide. Any scavengers present are removed by a simple extraction procedure which on lyophilization of the aqueous phase affords the crude peptide free of scavengers. Reagents for peptide synthesis are generally available from Calbiochem-Novabiochem (UK) Ltd, Nottingham NG7 2QJ, UK.

Purification may be effected by any one, or a combination of, techniques such as size exclusion chromatography, ion-exchange chromatography and (usually) reverse-phase high performance liquid chromatography.

Analysis of peptides may be carried out using thin layer chromatography, reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

In a further preferred embodiment thereof, the invention provides a collagen binding peptide, wherein said peptide is a fusion protein. Fusion proteins and methods for their construction are well known in the state of the art and can include genetic fusion of the peptide with an enzyme group (e.g. producing a color signal), a tag for purification (e.g. a His-tag), a chelating peptide, and the like.

In another aspect of the present invention, there are also provided antisera and an antibody or fragment thereof that is immunologically reactive with the collagen binding peptide of the present invention which also can be utilized in methods of treatment which involve inhibition of the attachment of the collagen binding peptide to collagen. In particular, specific polyclonal antiserum or an antibody or fragment thereof against the collagen binding peptide could be generated that reacts with the collagen binding peptide in, for example, Western immunoblots and ELISA assays and which interferes with the binding of the peptide to collagen. This antiserum or an antibody or fragment thereof can thus be used for specific agglutination assays to detect bacteria which express a collagen binding peptide. Preferred in the context of the present invention is a monoclonal antibody that selectively (specifically) binds to the collagen binding peptide of the present invention, more particularly and preferably selectively to a peptide according to any of the sequence according to SEQ ID No. 1 to SEQ ID No. 15. Most preferred is a monoclonal antibody which immunologically recognizes all of the sequences according to SEQ ID No. 1 to SEQ ID No. 15, and preferably specifically recognizes all of the sequences according to SEQ ID No. 1 to SEQ ID No. 15.

A "fragment" of a ligand, in particular a fragment of an antibody, shall mean a moiety that is derived from the ligand that is still capable of binding to the respective cellular marker (for example, the collagen binding peptide). Particular examples for antibodies are scFV-fragments and other antibody-derived peptides that can bind to the respective cellular marker. In a preferred embodiment, the binding of the fragment leads to the same biological effect(s) as the binding of the full-length (or sized) ligand, preferably the inhibition of the collagen-binding of the peptide according to the invention.

Modifications and changes may be made in the structure of the peptides of the present invention and DNA segments which encode them and still obtain a functional molecule that encodes a protein or peptide with desirable characteristics. The amino acids changes may be achieved by changing the codons of the DNA sequence. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In addition, amino acid substitutions are also possible without affecting the collagen binding ability of the isolated peptides of the invention, provided that the substitutions provide amino acids having sufficiently similar properties to the ones in the original sequences.

Accordingly, acceptable amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The isolated peptides of the present invention can be prepared in a number of suitable ways known in the art including typical chemical synthesis processes to prepare a sequence of polypeptides.

A further aspect of the invention provides a nucleic acid (e.g. polynucleotide) encoding a peptide of the invention. The nucleic acid according to the present invention may be DNA, cDNA, PNA, CNA, RNA or combinations thereof and it may or may not contain introns as long as it codes for the peptide. Of course, only peptides which contain naturally occurring amino acid residues joined by naturally occurring peptide bonds are encodable by a polynucleotide. A still further aspect of the invention provides an expression vector capable of expressing a polypeptide according to the invention.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) Science 239, 487-491. This method may be used for introducing the DNA into a suitable vector, for example by engineering in suitable restriction sites, or it may be used to modify the DNA in other useful ways as is known in the art. In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

The present invention also relates to a host cell transformed with a polynucleotide vector construct of the present invention. The host cell can be either prokaryotic or eukaryotic.

Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) Proc. Natl. Acad. Sci. USA 69, 2110 and Sambrook et al (1989) Molecular Cloning, A Laboratory Manual, Cold Spring Harbor Laboratory, Cold Spring Harbor, N.Y. Transformation of yeast cells is described in Sherman et al (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) J. Mol. Biol. 98, 503 or Berent et al (1985) Biotech. 3, 208. Alternatively, the presence of the protein in the supernatant can be detected using antibodies as described below.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells, as above.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention. Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

In another aspect of the present invention, the present invention provides an improved method for screening for ligands of the collagen binding peptide according to the present invention, comprising the steps of: a) incubating said peptide with a putative ligand, b) measuring a binding between said peptide and said putative ligand, and c) identifying said ligand. Preferably, the ligand inhibits or substantially inhibits collagen binding of said peptide.

In one embodiment, these ligands can be identified based on the structural similarities of the collagen-binding peptide with other proteins. Examples for the generation of such ligands are described in the literature (as mentioned also herein) and well known to the person of skill.

During the course of the assay of the method according to the invention, the ligand will initially bind or attach to the collagen binding peptide. The ligand can either bind directly or indirectly to the collagen binding peptide, i.e. via cofactors that can be present, such as certain ions or protein factors, that promote the attachment of the ligand to the collagen binding peptide, and therefore support the function of the ligand. "Binding" can occur via a covalent or non-covalent attachment of the ligand or group of ligands to the collagen binding peptide. Based on the binding properties of the screened ligands, a first pre-selection of ligands can be performed, in which a non-binding ligand is screened in a second "round" of screening using a set of co-factors. If still no binding occurs, the ligand will be classified as "non-binding" and disregarded in further screenings. Such pre-selection will be encompassed by the terms "screening", "measuring" and/or "determining" in the general context of this invention. A ligand that shows an in-vitro action should in vivo preferably not further interact with components of the patients' or test (model) organisms' body, e.g. within the bloodstream, lung and/or heart of the patient or test organism.

In general, assays to determine a binding and biological effect of a ligand to a specific target (in this case the collagen binding peptide) are well known to the person skilled in the art and can be found, for example, in U.S. Pat. Nos. 4,980, 281, 5,266,464 and 5,688,655 to Housey for phenotypic changes of cells after incubation with a screening ligand. Furthermore, U.S. Pat. No. 5,925,333 to Krieger at al. describes methods for modulation of lipid uptake and related screening methods.

Suitable tests for showing a biological effect of a ligand for the collagen binding peptide may include lytic assays that measure the release of intracellular contents (uric acid, potassium, phosphorus) into the extracellular compartment, fluorescence based assays (e.g. use of confocal fluorescent microscopy), viable cell counts, cellular proliferation assays, such as the BrdU proliferation assay or measuring of cellular calcium, and the like.

The method of screening according to the present invention can be performed in several different formats. One embodiment is a method, wherein the assay is performed in vitro. The screening assays of the present invention preferably involve the use of host cell-lines (as described above) and other cells, as long as these cells express the collagen binding peptide. How to produce such recombinant cells is well known to the skilled artisan and is further described above and in the respective literature.

An additional embodiment of the present invention relates to a method wherein the assay is performed in vivo. Preferably, the assay is performed in a mouse or rat. In general, the in vivo assay will not be substantially different from the above-mentioned in vitro assay. In a general screening assay for ligands of the collagen binding peptide will be provided in that the ligand to be tested is/are administered to a mouse or a rat. Then, it will be determined, if said ligand leads to an inhibition of the collagen binding activity, compared to the absence of the ligand to be tested, wherein a difference identifies a ligand which leads to an inhibition or reduction of the collagen binding activity. Of course, these assays can be performed in other non-human mammals as well.

An additional embodiment of the present invention relates to a method according to the invention, wherein said ligand is selected from a library of naturally occurring or synthetic compounds which are randomly tested for binding to the collagen binding peptide. Such libraries and the methods how to build up such a library, as well as methods for using these libraries for the screening of candidate ligands are well known to the person skilled in the art and further described in the respective literature. Furthermore, some of these libraries are commercially available. The present invention contemplates high throughput screening of ligands for the collagen binding peptide. The ligands as described above, and modifications of said ligands, including analogues, derivatives, fragments, active moieties, and the like, may be screened using methods and systems of the present invention.

In a further preferred embodiment of the method for screening according to the present invention, said ligand is an antibody or fragment thereof that is immunologically reactive with the collagen binding peptide as described above.

In another preferred aspect of the present invention, the collagen binding peptides, or active fragments thereof, are useful in a method for screening compounds to identify compounds that inhibit collagen binding of streptococci to host molecules. In accordance with the method, the compound of interest is combined with one or more of the collagen binding peptides or fragments thereof and the degree of binding of the protein to collagen or other extracellular matrix proteins is measured or observed. If the presence of the compound results in the inhibition of protein-collagen binding, for example, then the compound may be useful for inhibiting streptococci in vivo or in vitro. The method could similarly be used to identify compounds that promote interactions of streptococci with host molecules. The method is particularly useful for identifying compounds having bacteriostatic or bacteriocidal properties.

For example, to screen for streptococcus agonists or antagonists, a synthetic reaction mixture, a cellular compartment (such as a membrane, cell envelope or cell wall) containing one or more of the collagen binding peptides or fragments thereof and a labeled substrate or ligand of the protein is incubated in the absence or the presence of a compound under investigation. The ability of the compound to agonize or antagonize the protein is shown by a decrease in the binding of the labeled ligand or decreased production of substrate product. Compounds that bind well and increase the rate of product formation from substrate are agonists. Detection of the rate or level of production of product from substrate may be enhanced by use of a reporter system, such as a colorimetric labeled substrate converted to product, a reporter gene that is responsive to changes in the collagen binding peptide nucleic acid or protein activity, and binding assays known to those skilled in the art. Competitive inhibition assays can also be used.

Potential antagonists include small organic molecules, peptides, polypeptides and antibodies that bind to the collagen binding peptide nucleic acid molecules or proteins or portions thereof and thereby inhibit their activity or bind to a binding molecule (such as collagen to prevent the binding of the collagen binding peptide nucleic acid molecules or proteins to its ligand. For example, a compound that inhibits the collagen binding peptide activity may be a small molecule that binds to and occupies the binding site of the collagen binding peptide, thereby preventing binding to cellular binding molecules, to prevent normal biological activity.

Examples of small molecules include, but are not limited to, small organic molecule, peptides or peptide-like molecules. Other potential antagonists include antisense molecules. Preferred antagonists include compounds related to and variants or derivatives of the collagen binding peptides or portions thereof. The nucleic acid molecules described herein may also be used to screen compounds for antibacterial activity.

Another preferred embodiment of the present invention relates to a method for the production of a pharmaceutical formulation, comprising the steps of: a) performing a screening method as above, and b) formulating the ligand as identified with a pharmaceutically acceptable carrier and/or excipient. Such formulations therefore include, in addition to the ligand/antibody, a physiologically acceptable carrier or diluent, possibly in admixture with one or more other agents such as other antibodies or drugs, such as an antibiotic. Suitable carriers include, but are not limited to, physiological saline, phosphate buffered saline, phosphate buffered saline glucose and buffered saline. Alternatively the ligand, e.g. the antibody, may be lyophilized (freeze dried) and reconstituted for use when needed by the addition of an aqueous buffered solution as described above. Routes of administration are routinely parenteral, including intravenous, intramuscular, subcutaneous and intraperitoneal injection or delivery. The administration can be systemic and/or locally.

Preferred pharmaceutical compositions according to the present invention comprise at least one peptide according to the present invention, an antibody according to the present invention, a nucleic acid according to the present invention or an expression vector according to the present invention, and a pharmaceutically acceptable carrier as above.

The object of the present invention is also solved by providing a pharmaceutical preparation, preferably in the form of a vaccine, that is effective against rheumatic fever, comprising an effective amount of a peptide according to the invention, or comprising a nucleic acid encoding such a peptide. The vaccine can furthermore contain additional peptides and/or excipients to be more effective, as is explained herein.

Preferably, the vaccine of the present invention contains a mutant of the peptide of the present invention, wherein the peptide has been inactivated in its collagen-binding activity, preferably its binding activity to human collagen, in order to avoid or substantially avoid the collagen binding of said peptide in vivo. Of course, these peptide(s) will still have an epitope structure that allows for the generation of anti-peptide antibodies that are also effective against the PARF-containing bacterial proteins and peptides. Examples for peptides that have been inactivated are those mutants as described and examined in the present examples and the Figures below, in particular in FIG. 4F (substituents $A^{58}$, $Y^{60}$, $L^{64}$, $N^{65}$, $LND^{66}$ and $YL^{61}$). The inactivated peptides can be used for an improvement of vaccines. The inactivation of the PARF-sequence through the substitution of amino acids shall reduce the risk of an induction of an autoimmune reaction against collagen. In order to ensure the protectivity of the vaccine the inactive form should remain as homologous as possible to the PARF-sequence. Single substitutions in positions 3, 7 or 8 of AXYLZZLN appear to be effective and are preferred. Position 1 has proven to be comparably tolerant.

Suitable carriers include, but are not limited to, physiological saline, phosphate buffered saline, phosphate buffered saline glucose and buffered saline. Alternatively the ligand, e.g. the antibody, may be lyophilized (freeze dried) and reconstituted for use when needed by the addition of an aqueous buffered solution as described above. Routes of administration are routinely parenteral, including intravenous, intramuscular, subcutaneous and intraperitoneal injection or delivery. The administration can be systemic and/or locally.

The vaccine may be administered without adjuvant. Preferably, the pharmaceutical composition according to the present invention further comprises at least one suitable adjuvant, such as BCG or alum. Other suitable adjuvants include Aquila's QS21 stimulon (Aquila Biotech, Worcester, Mass., USA) which is derived from saponin, mycobacterial extracts and synthetic bacterial cell wall mimics, and proprietory adjuvants such as Ribi's Detox. Quil A, another saponin derived adjuvant, may also be used (Superfos, Denmark). Other adjuvants such as CpG oligonucleotides, stabilized RNA, Imiquimod (commercially available under the tradename Aldara™ from 3M Pharma, U.S.A.), Incomplete Freund's Adjuvant (commercially available as Montanide ISA-51 from Seppic S.A., Paris, France), liposomal formulations may also be useful. It may also be useful to give the peptide conjugated to keyhole limpet hemocyanin, preferably also with an adjuvant.

As already mentioned briefly above, the object of the present invention, in a further aspect thereof, is solved by a pharmaceutical composition that contains at least one collagen binding peptide according to SEQ ID No. 1 to SEQ ID No. 15 according to the invention, a nucleic acid according to the invention, an antibody according to the invention, or an expression vector according to the invention, and a pharmaceutically acceptable carrier. This composition is used for parenteral administration, such as subcutaneous, intradermal, intraperitoneal, intravenous, intramuscular or oral administration. For this, the peptides are dissolved or suspended in a pharmaceutically acceptable, preferably aqueous carrier. In addition, the composition can contain excipients, such as buffers, binding agents, blasting agents, diluents, flavors, lubricants, etc. The peptides can also be administered together with immune stimulating substances, such as cytokines. An extensive listing of excipients that can be used in such a composition, can be, for example, taken from A. Kibbe, Handbook of Pharmaceutical Excipients, 3. Ed., 2000, American Pharmaceutical Association and pharmaceutical press. The composition can be used for a prevention, prophylaxis and/or therapy of bacterial, and in particular streptococcal diseases.

The pharmaceutical preparation of the present invention, containing at least one of the peptides of the present invention comprising SEQ ID No. 1 to SEQ ID No. 15, a nucleic acid according to the invention, an antibody of the present invention, or an expression vector according to the invention, is administered to a patient that suffers from a bacterial, and in particular streptococcal disease, in particular rheumatic fever.

In general, the peptides that are present in the pharmaceutical composition according to the invention have the same properties as described above for peptides of the present invention comprising SEQ ID No. 1 to SEQ ID No. 15. Thus, they can have an overall length of between 8 and 100, preferably between 8 and 30, and most preferred between 8 and 12 amino acids. Furthermore, at least one peptide according to any of SEQ ID No. 1 to SEQ ID No. 15 can include non-peptide bonds. Furthermore, the respective nucleic acids can encode for between 8 and 100, preferably between 8 and 30, and most preferred between 8 and 12 amino acids. Most preferred is a pharmaceutical composition according to the invention that comprises a peptide consisting of amino acid sequences according to SEQ ID No. 1 to SEQ ID No. 15.

The pharmaceutical preparation, containing at least one of the peptides of the present invention comprising any of SEQ ID No. 1 to SEQ ID No. 15 is administered to a patient that suffers from a bacterial disease that is associated with the respective peptide according to the invention. Thereby, a peptide-specific immune response can be triggered.

The dosage of the ligand of the collagen binding peptide, preferably the anti-collagen binding motif antibody, to be administered to a patient suffering from the present diseases will vary with the precise nature of the condition being treated and the recipient of the treatment. The dose will generally be in the range of about 0.1 to about 100 mg for an adult patient, usually administered daily for a period between 1 and 30 days. The preferred daily dose is 1 to 10 mg per day, although in some instances larger doses of up to 40 mg per day may be used. Preferably the dosage will be applied in such a manner that the ligand is present in the medicament in concentrations that provide in vivo concentrations of said ligand in a patient to be treated of between 0.01 mg/kg/day and 1 mg/kg/day.

Another aspect of the present invention relates to the peptide according to the present invention, the antibody according to the present invention, the nucleic acid according to the present invention, or the expression vector according to the present invention or the pharmaceutical composition according to the present invention for use in medicine. Preferred is a use of the pharmaceutical composition according to the present invention as an anti-rheumatic fever vaccine, as described above Another aspect of the present invention relates to the use of a peptide according to the present invention, the antibody according to the present invention, the nucleic acid according to the present invention, or the expression vector according to the present invention, or the pharmaceutical composition according to the present invention for the manufacture of a medicament for the prevention and/or treatment of streptococcal infections and/or rheumatic fever and/or rheumatic heart disease.

Yet another important aspect of the present invention relates to a method for diagnosing a streptococcus, a streptococcal infection, rheumatic fever and/or rheumatic heart disease, comprising the steps of a) obtaining a sample from a patient to be diagnosed, and b) detecting the presence and/or the amount of a peptide according to the present invention, an antibody according to the present invention, and/or a nucleic acid according to the present invention in said sample. Further details regarding the diagnosis are well known to the person of skill, and are also described below.

Yet another important aspect of the present invention relates to a diagnostic kit for diagnosing a streptococcus, a streptococcal infection, rheumatic fever and/or rheumatic heart disease, comprising a peptide according to the present invention, an antibody according to the present invention, and/or a nucleic acid according to the present invention, optionally together with suitable labels and dyes.

The invention thus further contemplates a kit containing one or more nucleic acid probes that are specific for the nucleic acids of the present invention, and which can be used for the detection of collagen-binding proteins from bacteria, and in particular of M- and M-like proteins in a sample, or for the diagnosis of related bacterial infections. Such a kit can also contain the appropriate reagents for hybridizing the probe to the sample and detecting bound probe. In an alternative embodiment, the kit contains antibodies specific to the peptide and/or peptides according to the present invention which can be used for the detection of collagen-binding proteins from bacteria, and in particular of M- and M-like proteins as described above.

In yet another embodiment, the kit contains one or more, or all of the collagen-binding proteins, or fragments thereof, which can be used for the detection of bacteria or for the presence of antibodies to collagen-binding bacterial proteins in a sample. The kits described herein may additionally contain equipment for safely obtaining the sample, a vessel for containing the reagents, a timing means, a buffer for diluting the sample, and a colorimeter, reflectometer, or standard against which a color change may be measured.

In a preferred embodiment, the reagents, including the protein or antibody, are lyophilized, most preferably in a single vessel. Addition of aqueous sample to the vessel results in volatilization of the lyophilized reagents, causing them to react. Most preferably, the reagents are sequentially lyophilized in a single container, in accordance with methods well known to those skilled in the art that minimize reaction by the reagents prior to addition of the sample.

Also provided herein are sequences of nucleic acid molecules that selectively hybridize with nucleic acid molecules encoding the collagen-binding proteins of the invention, or portions thereof, such as consensus amino acid motif, as described herein or complementary sequences thereof. By "selective" or "selectively" is meant a sequence which does not hybridize with other nucleic acids. This is to promote specific detection of the collagen binding motif according to the invention. Therefore, in the design of hybridizing nucleic acids, selectivity will depend upon the other components present in a sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus, has the same meaning as "specifically hybridizing". The selectively hybridizing nucleic acids of the invention can have at least 70%, 80%, 85%, 90%, 95%, 97%, 98%, and 99% complementarity with the segment of the sequence to which they hybridize.

The invention contemplates sequences, probes and primers which selectively hybridize to the encoding DNA or the complementary, or opposite, strand of DNA as those specifically provided herein. Specific hybridization with nucleic acid can occur with minor modifications or substitutions in the nucleic acid, so long as functional species-specific hybridization capability is maintained. By "probe" is meant nucleic acid sequences that can be used as probes or primers for selective hybridization with complementary nucleic acid sequences for their detection or amplification, which probes can very in length from about 5 to 100 nucleotides, or preferably from about 10 to 50 nucleotides, or most preferably about 18-24 nucleotides. Therefore, the terms "probe" or "probes" as used herein are defined to include "primers". Isolated nucleic acids are provided herein that selectively hybridize with the species-specific nucleic acids under stringent conditions and should have at least 5 nucleotides complementary to the sequence of interest as described by Sambrook et al., 1989. Molecular Cloning: A Laboratory Manual, 2nd ed. Cold Spring Harbor Laboratory, Cold Spring Harbor, N.Y.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of diagnosing the presence of the *S. pyogenes*, the degree of complementarity between the hybridizing nucleic acid (probe or primer) and the sequence to which it hybridizes (e.g., group A streptococcal DNA from a sample) is at least enough to distinguish hybridization with a nucleic acid from other bacteria.

The present invention provides a method for the prevention and/or treatment of a human subject suffering from a streptococcal infection and/or rheumatic fever and/or rheumatic heart disease, which comprises administering to the said subject an effective amount of an agent selected from a peptide according to the invention, an antibody according to the invention, a nucleic acid according to the invention, an expression vector according to the invention, or the pharmaceutical composition according to the invention. Preferred is an antibody recognizing the collagen binding peptide and motif according to the invention. Suitable formulations, routes of administrations and dosages are indicated above and are further laid out in the following examples. Most preferred is the treatment as an anti-rheumatic fever vaccine.

The eradication of the carriage of streptococci other than *S. pyogenes* appears to be important for prevention of rheumatic fever. Moreover, the presence of PARF in colonizing bacteria appears to be an important marker and its identification by a specific diagnostic test also represents a novel strategy to control acute rheumatic fever and subsequent rheumatic heart disease.

It should be understood that the features of the invention as disclosed and described herein can be used not only in the respective combination as indicated but also in a singular fashion without departing from the intended scope of the present invention.

The invention will now be described in more detail by reference to the following Figures, the Sequence listing, and the Examples. The following examples are provided for illustrative purposes only and are not intended to limit the invention.

SEQ ID No 1 to SEQ ID No 15 show peptide sequences of collagen binding peptides according to the present invention.

FIG. 1 shows the binding of radiolabeled collagen IV to GCS and GGS isolates from animal and human infections. (A) The percentage of collagen binding strains. (B) Isolates found positive for collagen-binding were tested for the presence of emm and emm-like genes by PCR, using primers of highly conserved sequences (black bar) and the presence of fog was determined by sequencing of the obtained PCR products (hatched bar).

Figure 2:
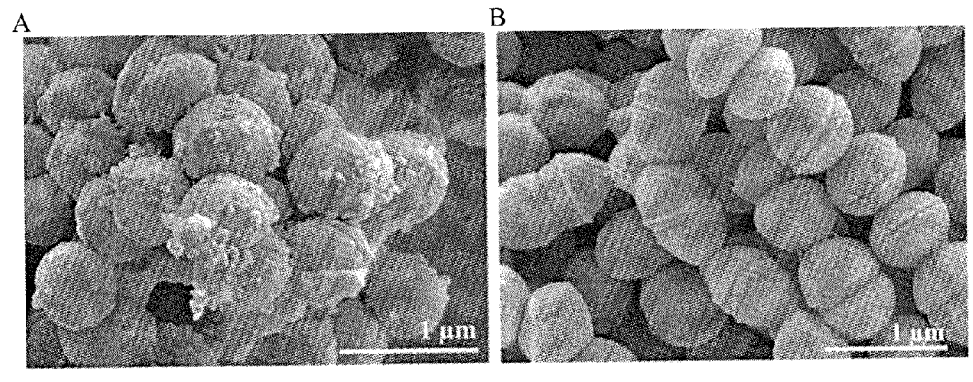
Figure 2:
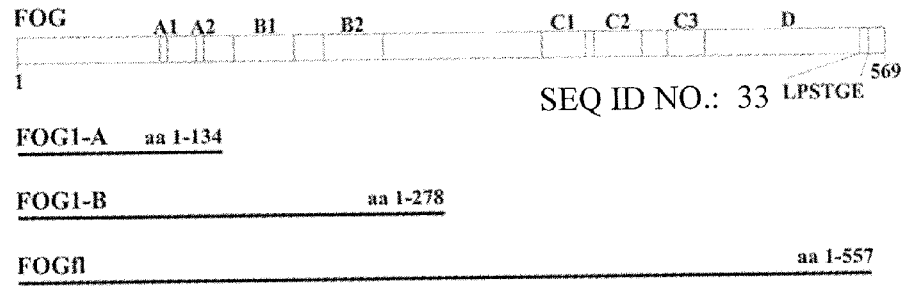
Figure 2:
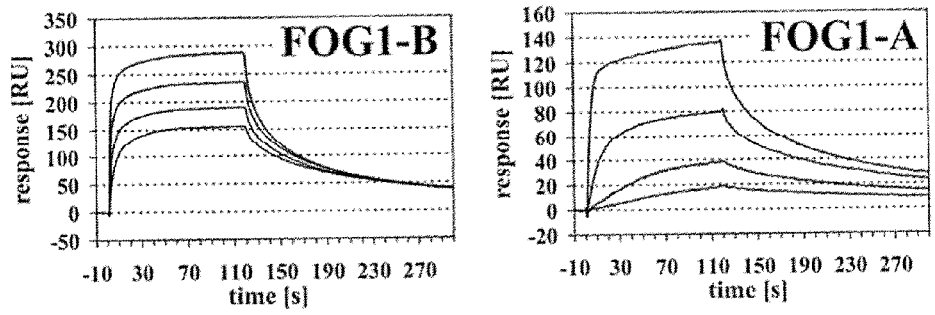

FIG. 2 shows streptococcal FOG as a collagen binder. SEM (Scanning Electron Micrograph) of FOG-expressing strain G45 (A) and of a FOG-negative non-collagen binding strain G50 (B), which were incubated with soluble collagen IV. (C) Schematic model of FOG depicting its domain composition and recombinant constructs. (D+E) Surface plasmon resonance measurement at different concentrations (12.5 µg/ml; 25 µg/ml; 50 µg/ml; 100 µg/ml) of FOG1-B and FOG1-A, respectively, using collagen IV as the immobilized ligand.

Figure 3:
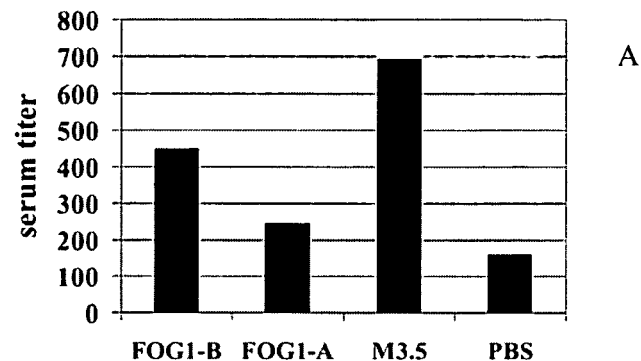
Figure 3:
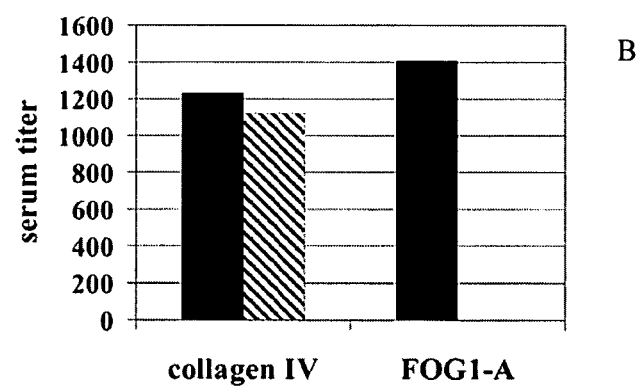
Figure 3:
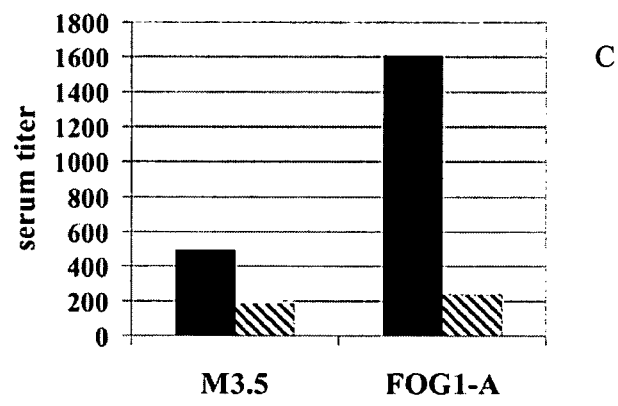

FIG. 3 shows autoimmune response against collagen IV induced by FOG and M3—(A) Mean serum titer against collagen IV of mice immunized with FOG1-B. FOG1-A, M3.5, or PBS, respectively. (B) Serum titer against collagen IV and FOG1-A of a pool of collagen IV reactive mouse sera determined prior to (black bar) and after pre-absorption with FOGfl-sepharose (hatched bars). (C) Sera of healthy volunteers (n=15, hatched bars) and of patients with ARF (n=7, black bars) were tested for reactivity against M3.5 or FOG1-A, respectively.

FIG. 4 shows the identification of PARF as collagen binding motif—(A) depicts a spot-membrane experiment with radiolabeled collagen IV as soluble ligand. Spots 1 to 40 are immobilized 15mer peptides constituting a 3 amino acid (aa)-shift representing the first 132 aa of the FOG-protein. Strong signals were obtained with peptide 17 to 20 (SEQ ID NOs: 16-19), the sequences of which are displayed in (B). The box indicates the amino acid motif that is present in all four peptides. The mutational analysis based on peptide 19 is depicted in (C). Mutations in the given peptide sequences (SEQ ID NOs:20-29) are indicated in bold and underlined letters. In peptide 50 the sequence from aa 58 to aa 166 was rearranged arbitrarily. In (D) peptide 19 is shown together with its position in the mature protein (superscript) (SEQ ID NO:30). Amino acids found to be crucial for collagen IV binding in the spot membrane experiments are indicated in bold letters. An alignment of protein FOG1-A (SEQ ID NO:31) and M3 (SEQ ID NO:32) identifies the homologous sequences shown in (E). The respective sequence of FOG is present in peptide 19. This region was subjected to site directed mutagenesis. Performed substitutions in FOGfl and the results of binding experiments using dot blot and SPR are indicated in a table in (F). These experiments identified the consensus sequence (SEQ ID NO:2) given in (G).

EXAMPLES

Material and Methods
Bacterial Strains and Human Sera—
Group C and G Streptococci strains were collected worldwide with an emphasis on human isolates from the Northern Territory in Australia. The *S. pyogenes* control strain (A60) was obtained from the Institute for Medical Microbiology of the TU Aachen. Unless stated otherwise, streptococci were grown statically to late exponential phase in tryptic soy broth (TSB; Roth) at 37° C. Human sera from patients with acute rheumatic fever (validated by the Jones criteria) and of healthy volunteers were collected in the same geographical area.
Collagen-Binding Assays—
Streptococci were suspended in PBS to give $10^8$ bacteria per ml. Then, $2.5 \times 10^7$ bacteria were incubated with 30 ng (100,000 cpm) of $^{125}$I-labeled collagen IV isolated from placenta (Sigma, Germany) for 45 minutes at room temperature. Bacteria were harvested by centrifugation, washed in phosphate buffered saline (PBS) with 0.05% Tween 20 (PBST), and the pellet was measured in a gamma counter. Hyaluronic acid (HA) capsule $2.5 \times 10^7$ was detected by pre-incubating bacteria with either 20 µl (60 U) hyaluronidase (Applichem, Darmstadt, Germany) or just 20 µl PBS for 45 min at 37° C. The bacteria were washed three times in 1 ml PBS prior to the incubation with the radio-labelled collagen. Assays were performed in triplicates within each set of experiments, and experiments were repeated on different days.
Screening and Sequencing of Emm and Emm-Like Genes—
According to recommendations (http://www.cdc.gov/ncidod/biotech/strep/doc.htm), the chromosomal DNA of all collagen binding isolates was tested by PCR for the presence of emm and emm-like genes, using the mentioned primers 1 and 2. The obtained PCR products were subsequently sequenced using primer 1.
Screening for the Presence of Cne—
The chromosomal DNA of all isolates positive for collagen binding was tested by PCR for the presence of cne using the conditions and primers described in (G. H. Stollerman, Clin Immunol Immunopathol 61, 131 (November 1991)).
Electron Microscopy—
$5 \times 10^7$ bacteria of G45 (a FOG-positive, collagen-binding strain) and G50 (a non-collagen binding strain) suspended in 500 µl PBST were incubated with 10 µg of collagen IV at room temperature for 30 minutes. Samples were washed, fixed and processed for field emission scanning electron microscopy (FESEM) as described before (K. Dinkla et al., J Clin Invest 11 1, 1905 (June 2003)).

Recombinant Proteins and Site Directed Mutagenesis—
For cloning of FOG and M3 constructs, suitable PCR products were cloned into the pGEX-6P-1 vector, between the BamHI and the SalI or the BamHI and the EcoRI cleavage site. FOGfl (amino acid residues 1-557) represents the mature full length protein. FOG1-B represents the first 278 amino acids, FOG1-A the first 134 amino acids of the mature FOG protein (FIG. 2C). The plasmids coded for fusion proteins that carried an aminoterminal GST-tag. They were expressed in *E. coli* HB101.
Site directed mutagenesis was performed on the plasmid pGEX-6P-1-FOGfl that coded for the GST-FOGfl fusion protein. *E. coli* clones containing the plasmids with the desired substitutions were generated using the GeneTailor™ Site Directed Mutagenesis System (Invitrogen) following the manufacturers recommendations. The tagged proteins from *E. coli* lysates were bound to glutathione sepharose 4B (GE Healthcare) and eluted with 10 mM reduced L-glutathione (Sigma) in 50 mM TrisHCl (pH=8.0) after washing the matrix with PBS. Alternatively, for SPR measurements of FOG1-B and FOG1-A the GST-tag was removed by digesting the proteins with PreScission™ protease (GE Healthcare) while bound to the affinity matrix, which eluted the untagged FOG proteins.
Immunization of Mice—
Pathogen free 8 week old female BALB/c mice were immunized intra-peritoneally with an emulsion of 25-30 µg recombinant purified protein in 50 µl PBS and 50 µl Freund's incomplete adjuvant per dose at day 1, 7 and 14. Control mice were injected with 50 µl PBS and 50 µl Freund's incomplete adjuvant per dose. At day 21, serum samples of each group were collected and tested in ELISA. To absorb FOG reactive antibodies, 10 µl serum pool was diluted 1:50 in PBS, and incubated for 1 h with 1 mg GST-FOGfl protein immobilized on glutathione sepharose 4B. Antibodies that bound to the affinity matrix were removed by centrifugation. The supernatant was subjected to ELISA analysis.
Enzyme Linked Immunosorbent Assay (ELISA)—
To determine anti-collagen CIV antibody titers, 96 well plates (Greiner, Frickenhausen, Germany) were coated over night at 4° C. with anti-human collagen IV rabbit polyclonal antibody (Progen, Heidelberg, Germany) diluted 1:100 in 0.1 M $NaHCO_3$ (pH=9.6), blocked with 2% bovine serum albumin (BSA) in PBST and incubated with collagen IV (2 µg/ml in PBS) for 1 h at 37° C. After washing with PBST, mouse sera or human sera diluted 1:50, 1:158, 1:500, and 1:1580 in PBS were added to the wells and incubated over night at 4° C. After washing, bound antibodies were detected using suitable horseradish peroxidase coupled secondary anti-serum (goat anti-mouse IgG,M, Jackson Laboratories; rabbit anti-human IgG, A, M, Sigma-Aldrich) and 2,2-azino-di-[3-ethylbenzthiazoline sulfonate]diammonium salt (ABTS tablets, Boehringer, Mannheim, Germany) as substrate. The absorbance was determined at 405 nm.
To determine anti-M3 or anti-FOG antibody titers, M3.5 or FOG (4 µg/ml in 0.1 M $NaHCO_3$, pH=9.6) were immobilized over night at 4° C., followed by blocking with 1% BSA in PBST. Wells were washed, before human sera diluted 1:100, 1:316, 1:1000, and 1:3162 in 1% BSA in PBS were added to the wells and incubated for 1.5 h at 37° C. Antibody binding was measured as described above.
Dot Blots—
Ligand overlay assays were performed by spotting the purified recombinant proteins (5 µg, or 0.5 µg) on nitrocellulose. The membrane was blocked for 1 h in PBS containing 5% skimmed milk, followed by a 1 h incubation with radiolabeled collagen IV (200,000 cpm) in PBST. After five washing steps in PBST, filters were dried and placed on radiographic films (Kodak) for autoradiography.

Surface Plasmon Resonance Measurements—

Protein interactions were studied in a BIAcore 2000 system (BIAcore AB) using 10 mM HEPES, 100 mM NaCl, pH=7.4 as running buffer. A CM5 sensor chip was activated by a 4 min injection of 0.05M N-hydroxysuccinimid, 0.2 M N-ethyl-N-(3-dimethylaminopropyl)-carbodiimide hydrochloride in water. Collagen IV from human placenta (Sigma, 1 mg/ml in 0.1M NaAc) was diluted 1:25 in 10 mM NaAc (pH=5.2). Immediate injection of 3 µl at a flow rate of 5 µl/min lead to immobilization of 400 to 550 response units (RU) of collagen IV. Residual reactive groups were inactivated by 6 min injection of 1 M ethanolamine, 0.1 M NaHCO$_3$, 0.5 M NaCl, 5 mM EDTA, pH=8.0. Interaction measurements with FOG1-A and FOG1-B were carried out at a flow rate of 60 µl/min measurements with GST-FOGfl, mutated GST-FOGfl, and GST at a flow rate of 35 µl/min. Surface regeneration was achieved by injection of two 30 s pulses of 0.2% SDS in water. The BIAevaluation 3.0 software was used for further analysis of the data. Shown curves represent the difference between the signal of the collagen-coupled surface and of a deactivated control surface devoid of protein. They were further corrected by subtraction of the curve that was obtained after injection of buffer alone. Buffer injection led to responses less than 5 RU.

Spot Synthesized Peptides—

The 15-mer peptides were synthesized on an aminopegylated cellulose membrane (AIMS Scientific Products, Germany) as described previously (R. Frank, Tetrahedron 48, 9217 (1992)). After washing in ethanol (96%) and thereafter in PBS the membrane was incubated for 1 h with blocking buffer (2% blocking solution from Genosys and 0.5% sucrose in PBST) at room temperature. Binding was tested by incubating the membrane with 3 µg of radiolabeled collagen IV (1,000,000 cpm) in PBST for 4 h at room temperature. Non-bound ligand was removed by washing with PBST for 1 h. Bound collagen IV was detected using an X-ray film.

The invention claimed is:

1. An isolated antibody or scFV-fragment thereof that specifically binds to a collagen binding amino acid sequence $AX^1YLX^2X^3X^4N$ (SEQ ID No. 1) wherein $X^1$ is selected from R, E or N; $X^2$ is K; $X^3$ is G, K or R; and $X^4$ is L; of a collagen binding peptide; wherein said peptide has between 8 and 100 amino acids; and wherein said antibody or scFV-fragment thereof inhibits the attachment of said collagen binding peptide to collagen.

2. A pharmaceutical composition comprising at least one antibody or fragment thereof according to claim 1, and a pharmaceutically acceptable carrier.

3. The pharmaceutical composition according to claim 2, further comprising at least one suitable adjuvant.

4. The antibody or fragment thereof according to claim 1, wherein said collagen binding peptide consists of the amino acid sequence selected from SEQ ID No. 4, 7, 9 and 10.

5. The antibody or fragment thereof according to claim 1, wherein said collagen binding peptide includes non-peptide bonds.

6. The antibody or fragment thereof according to claim 1, wherein said collagen binding peptide is part of a fusion protein.

* * * * *

UNITED STATES PATENT AND TRADEMARK OFFICE
CERTIFICATE OF CORRECTION

PATENT NO. : 8,956,612 B2
APPLICATION NO. : 12/302969
DATED : February 17, 2015
INVENTOR(S) : Gursharan S. Chhatwal et al.

It is certified that error appears in the above-identified patent and that said Letters Patent is hereby corrected as shown below:

Title Page

Item (57), Abstract,
Line 3, "designated as peptide" should read --designated as a peptide--.

In the Specification

Column 1,
Line 12, "designated as peptide" should read --designated as a peptide--.
Line 48, "strains. which" should read --strains, which--.

Column 2,
Line 25, "is describes" should read --is described--.

Column 3,
Line 34, "thereof The" should read --thereof. The--.
Lines 39-40, "as collagen" should read --as the collagen--.

Column 5,
Line 4, "collagen is the" should read --collagen are the--.
Line 21, "was investigated." should read --were investigated.--.
Line 44, "In case of" should read --In the case of--.
Lines 61-62, "against N-terminal" should read --against the N-terminal--.
Line 66, "of FOG" should read --of the FOG--.

Column 6,
Line 5, "peptide 17 to 20" should read --peptides 17 to 20--.
Line 36, "In both, FOG and" should read --In both FOG and--.

Signed and Sealed this
First Day of September, 2015

Michelle K. Lee
*Director of the United States Patent and Trademark Office*

Line 52, "hat the induction' of" should read --that the induction of--.

Column 8,
Line 3, "peptide free" should read --peptide to be free--.

Column 14,
Line 2, "organic molecule," should read --organic molecules,--.

Column 18,
Line 40, "fog" should read --FOG--.
Line 61, "as collagen" should read --as a collagen--.
Line 66, "peptide 17 to 20" should read --peptides 17 to 20--.

Column 20,
Line 7, "FOG1-A the first" should read --FOG1-A represents the first--.
Line 16, "manufacturers" should read --manufacturer's--.
Line 49, "coupled secondary" should read --coupled with secondary--.

Column 21,
Line 12, "lead to" should read --led to--.

```
                        SEQUENCE LISTING

<160> NUMBER OF SEQ ID NOS: 33

<210> SEQ ID NO 1
<211> LENGTH: 8
<212> TYPE: PRT
<213> ORGANISM: Streptococcus sp.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 1

Ala Xaa Tyr Leu Xaa Xaa Leu Asn
1               5

<210> SEQ ID NO 2
<211> LENGTH: 8
<212> TYPE: PRT
<213> ORGANISM: Streptococcus sp.
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid,
      one of Xaa must be a basic amino acid, e.g. Arg or Lys

<400> SEQUENCE: 2

Ala Xaa Tyr Leu Xaa Xaa Leu Asn
1               5

<210> SEQ ID NO 3
<211> LENGTH: 8
<212> TYPE: PRT
<213> ORGANISM: Streptococcus sp.

<400> SEQUENCE: 3

Ala Arg Tyr Leu Gln Lys Leu Asn
1               5

<210> SEQ ID NO 4
<211> LENGTH: 8
```

```
<212> TYPE: PRT
<213> ORGANISM: Streptococcus sp.

<400> SEQUENCE: 4

Ala Glu Tyr Leu Lys Gly Leu Asn
1               5

<210> SEQ ID NO 5
<211> LENGTH: 8
<212> TYPE: PRT
<213> ORGANISM: Streptococcus sp.

<400> SEQUENCE: 5

Ala Glu Tyr Leu Gln Arg Leu Asn
1               5

<210> SEQ ID NO 6
<211> LENGTH: 8
<212> TYPE: PRT
<213> ORGANISM: Streptococcus sp.

<400> SEQUENCE: 6

Ala Glu Tyr Leu Gln Arg Leu Asn
1               5

<210> SEQ ID NO 7
<211> LENGTH: 8
<212> TYPE: PRT
<213> ORGANISM: Streptococcus sp.

<400> SEQUENCE: 7

Ala Trp Tyr Leu Lys Glu Leu Asn
1               5

<210> SEQ ID NO 8
<211> LENGTH: 8
<212> TYPE: PRT
<213> ORGANISM: Streptococcus sp.

<400> SEQUENCE: 8

Ala Arg Tyr Leu Glu Thr Leu Asn
1               5

<210> SEQ ID NO 9
<211> LENGTH: 8
<212> TYPE: PRT
<213> ORGANISM: Streptococcus sp.

<400> SEQUENCE: 9

Ala Glu Tyr Leu Lys Ala Leu Asn
1               5

<210> SEQ ID NO 10
<211> LENGTH: 8
<212> TYPE: PRT
<213> ORGANISM: Streptococcus sp.

<400> SEQUENCE: 10

Ala Thr Tyr Leu Lys Glu Leu Asn
1               5

<210> SEQ ID NO 11
<211> LENGTH: 8
<212> TYPE: PRT
<213> ORGANISM: Streptococcus sp.
```

```
<400> SEQUENCE: 11

Ala Gln Tyr Leu Arg Glu Leu Asn
1               5

<210> SEQ ID NO 12
<211> LENGTH: 8
<212> TYPE: PRT
<213> ORGANISM: Streptococcus sp.

<400> SEQUENCE: 12

Glu Ala Tyr Leu Lys Arg Leu Asn
1               5

<210> SEQ ID NO 13
<211> LENGTH: 8
<212> TYPE: PRT
<213> ORGANISM: Streptococcus sp.

<400> SEQUENCE: 13

Thr Gln Tyr Leu Lys Arg Leu Asn
1               5

<210> SEQ ID NO 14
<211> LENGTH: 8
<212> TYPE: PRT
<213> ORGANISM: Streptococcus sp.

<400> SEQUENCE: 14

Thr Gln Tyr Leu Lys Arg Leu Asn
1               5

<210> SEQ ID NO 15
<211> LENGTH: 8
<212> TYPE: PRT
<213> ORGANISM: Streptococcus sp.

<400> SEQUENCE: 15

Ala Arg Tyr Leu Lys Arg Leu Asn
1               5

<210> SEQ ID NO 16
<211> LENGTH: 15
<212> TYPE: PRT
<213> ORGANISM: Streptococcus sp.

<400> SEQUENCE: 16

Lys Gln Asn Asn Ser Ile Gly Glu Tyr Ala Arg Tyr Leu Gln Lys
1               5                   10                  15

<210> SEQ ID NO 17
<211> LENGTH: 15
<212> TYPE: PRT
<213> ORGANISM: Streptococcus sp.

<400> SEQUENCE: 17

Asn Ser Ile Gly Glu Tyr Ala Arg Tyr Leu Gln Lys Leu Asn Asp
1               5                   10                  15

<210> SEQ ID NO 18
<211> LENGTH: 15
<212> TYPE: PRT
<213> ORGANISM: Streptococcus sp.

<400> SEQUENCE: 18
```

Gly Glu Tyr Ala Arg Tyr Leu Gln Lys Leu Asn Asp Gln Phe Gln
1               5                   10                  15

<210> SEQ ID NO 19
<211> LENGTH: 15
<212> TYPE: PRT
<213> ORGANISM: Streptococcus sp.

<400> SEQUENCE: 19

Ala Arg Tyr Leu Gln Lys Leu Asn Asp Gln Phe Gln Glu Tyr Tyr
1               5                   10                  15

<210> SEQ ID NO 20
<211> LENGTH: 15
<212> TYPE: PRT
<213> ORGANISM: Streptococcus sp.

<400> SEQUENCE: 20

Gly Glu Tyr Ala Arg Tyr Leu Gln Lys Leu Asn Ala Gln Phe Gln
1               5                   10                  15

<210> SEQ ID NO 21
<211> LENGTH: 15
<212> TYPE: PRT
<213> ORGANISM: Streptococcus sp.

<400> SEQUENCE: 21

Gly Glu Tyr Ala Arg Tyr Leu Gln Lys Leu Ala Asp Gln Phe Gln
1               5                   10                  15

<210> SEQ ID NO 22
<211> LENGTH: 15
<212> TYPE: PRT
<213> ORGANISM: Streptococcus sp.

<400> SEQUENCE: 22

Gly Glu Tyr Ala Arg Tyr Leu Gln Lys Ala Asn Asp Gln Phe Gln
1               5                   10                  15

<210> SEQ ID NO 23
<211> LENGTH: 15
<212> TYPE: PRT
<213> ORGANISM: Streptococcus sp.

<400> SEQUENCE: 23

Gly Glu Tyr Ala Arg Tyr Leu Gln Ala Leu Asn Asp Gln Phe Gln
1               5                   10                  15

<210> SEQ ID NO 24
<211> LENGTH: 15
<212> TYPE: PRT
<213> ORGANISM: Streptococcus sp.

<400> SEQUENCE: 24

Gly Glu Tyr Ala Arg Tyr Leu Ala Lys Leu Asn Asp Gln Phe Gln
1               5                   10                  15

<210> SEQ ID NO 25
<211> LENGTH: 15
<212> TYPE: PRT
<213> ORGANISM: Streptococcus sp.

<400> SEQUENCE: 25

Gly Glu Tyr Ala Arg Tyr Ala Gln Lys Leu Asn Asp Gln Phe Gln

<210> SEQ ID NO 26
<211> LENGTH: 15
<212> TYPE: PRT
<213> ORGANISM: Streptococcus sp.

<400> SEQUENCE: 26

Gly Glu Tyr Ala Arg Ala Leu Gln Lys Leu Asn Asp Gln Phe Gln
 1               5                  10                  15

<210> SEQ ID NO 27
<211> LENGTH: 15
<212> TYPE: PRT
<213> ORGANISM: Streptococcus sp.

<400> SEQUENCE: 27

Gly Glu Tyr Ala Ala Tyr Leu Gln Lys Leu Asn Asp Gln Phe Gln
 1               5                  10                  15

<210> SEQ ID NO 28
<211> LENGTH: 15
<212> TYPE: PRT
<213> ORGANISM: Streptococcus sp.

<400> SEQUENCE: 28

Gly Glu Tyr Asp Arg Tyr Leu Gln Lys Leu Asn Asp Gln Phe Gln
 1               5                  10                  15

<210> SEQ ID NO 29
<211> LENGTH: 15
<212> TYPE: PRT
<213> ORGANISM: Streptococcus sp.

<400> SEQUENCE: 29

Gly Glu Tyr Arg Asp Leu Lys Leu Gln Ala Tyr Asn Gln Phe Gln
 1               5                  10                  15

<210> SEQ ID NO 30
<211> LENGTH: 15
<212> TYPE: PRT
<213> ORGANISM: Streptococcus sp.

<400> SEQUENCE: 30

Gly Glu Tyr Ala Arg Tyr Leu Gln Lys Leu Asn Asp Gln Phe Gln
 1               5                  10                  15

<210> SEQ ID NO 31
<211> LENGTH: 118
<212> TYPE: PRT
<213> ORGANISM: Streptococcus sp.

<400> SEQUENCE: 31

Asp Arg Trp Lys Ala Gln Thr Glu Glu Ala Arg Thr Asp Lys Leu Ile
 1               5                  10                  15

Ala Gly Phe Ala Asn Leu Asp Ala Asp Val Thr Asn Leu Gly Lys Met
                20                  25                  30

Met Asp Glu Leu Gln Lys Leu Lys Asp Phe Ser Lys Gln Asn Asn Ser
         35                  40                  45

Ile Gly Glu Tyr Ala Arg Tyr Leu Gln Lys Leu Asn Asp Gln Phe Gln
     50                  55                  60

Glu Tyr Tyr Glu Gln Val Val Gly Asp Asp Ser Arg Arg Val Leu Ala
65                  70                  75                  80

```
Lys Glu Leu Ala Lys Asn Thr Glu Leu Asn Glu Lys Leu Ser Glu Leu
                85                  90                  95

Ser Thr Thr Ser Gln Ala Leu Ala Lys Glu Leu Gln Glu Gln Lys Glu
                100                 105                 110

Asn Tyr Asp Leu Val Lys
            115

<210> SEQ ID NO 32
<211> LENGTH: 118
<212> TYPE: PRT
<213> ORGANISM: Streptococcus sp.

<400> SEQUENCE: 32

Asp Ala Arg Ser Val Asn Gly Glu Phe Pro Arg His Val Lys Leu Lys
1               5                   10                  15

Asn Glu Ile Glu Asn Leu Leu Asp Gln Val Thr Gln Leu Tyr Thr Lys
                20                  25                  30

His Asn Ser Asn Tyr Gln Gln Tyr Asn Ala Gln Ala Gly Arg Leu Asp
            35                  40                  45

Leu Arg Gln Lys Ala Glu Tyr Leu Lys Gly Leu Asn Asp Trp Ala Glu
        50                  55                  60

Arg Leu Leu Gln Glu Leu Asn Gly Glu Asp Val Lys Lys Val Leu Gly
65                  70                  75                  80

Lys Val Ala Phe Glu Lys Asp Leu Glu Lys Glu Val Lys Glu Leu
                85                  90                  95

Lys Glu Lys Ile Asp Lys Lys Glu Lys Glu Tyr Gln Asp Leu Asp Lys
                100                 105                 110

Asp Phe Asp Leu Ala Lys
            115

<210> SEQ ID NO 33
<211> LENGTH: 6
<212> TYPE: PRT
<213> ORGANISM: Streptococcus sp.

<400> SEQUENCE: 33

Leu Pro Ser Thr Gly Glu
1               5
```